United States Patent
Hu et al.

(10) Patent No.: US 7,302,035 B2
(45) Date of Patent: Nov. 27, 2007

(54) SCANNING ARM AND TRAIN INSPECTION SYSTEM BY IMAGING THROUGH RADIATION HAVING THE SCANNING ARM

(75) Inventors: Bin Hu, Beijing (CN); Shangmin Sun, Beijing (CN); Yucheng Wu, Beijing (CN); Nan Jiang, Beijing (CN); Zhizhong Liang, Beijing (CN); Wanquan Shen, Beijing (CN); Ning Li, Beijing (CN)

(73) Assignee: Nuctech Company Limited, Beijing (CN)

( * ) Notice: Subject to any disclaimer, the term of this patent is extended or adjusted under 35 U.S.C. 154(b) by 72 days.

(21) Appl. No.: 11/285,974

(22) Filed: Nov. 23, 2005

(65) Prior Publication Data

US 2006/0203962 A1    Sep. 14, 2006

(30) Foreign Application Priority Data

Nov. 26, 2004    (CN) .................... 2004 1 0009888

(51) Int. Cl.
    *G01N 23/04* (2006.01)
(52) U.S. Cl. .......................... 378/57; 378/62
(58) Field of Classification Search ............ 378/57–62; 248/618, 636, 638
    See application file for complete search history.

(56) References Cited

U.S. PATENT DOCUMENTS

| 4,841,554 | A | * | 6/1989 | Doenges et al. ............... 378/57 |
| 6,058,158 | A | * | 5/2000 | Eiler ............................. 378/57 |
| 6,129,198 | A | * | 10/2000 | Nusime ....................... 198/326 |
| 7,082,186 | B2 | * | 7/2006 | Zhao et al. .................... 378/57 |
| 2007/0133740 | A1 | * | 6/2007 | Kang et al. .................... 378/57 |

\* cited by examiner

*Primary Examiner*—Jurie Yun
(74) *Attorney, Agent, or Firm*—Knobbe Martens Olson & Bear LLP

(57) ABSTRACT

A train inspection system by imaging through radiation, having a scanning arm positioned away from the track and supported on a construction base, and vibration damping elements positioned between the scanning arm and the construction base. The system includes a detector bracket with detector arrays mounted thereon, a radiation source, a calibration device, a front collimator, and a rear collimator. The sector-shaped x-rays emitted from the radiation source penetrate through the calibration device, the front collimator, the rear collimator and the train to be inspected sequentially so as to be received by the detector arrays provided on the detector bracket.

4 Claims, 1 Drawing Sheet

SCANNING ARM AND TRAIN INSPECTION SYSTEM BY IMAGING THROUGH RADIATION HAVING THE SCANNING ARM

CROSS-REFERENCE TO RELATED APPLICATION

This application claims the benefit of Chinese Patent Application No. 200410009888.1 filed on Nov. 26, 2004 in the State Intellectual Property Office of China, the disclosure of which is incorporated herein by reference.

FIELD OF THE INVENTION

The present invention relates to a train inspection system by imaging through radiation, particularly to a scanning arm used for a train inspection system by imaging through radiation and capable of reducing vibration.

DESCRIPTION OF THE PRIOR ART

In the prior arts, the pulling type container inspection systems such as the large-scale container inspection systems manufactured by Heimann Corporation, Germany and the British Airspace Company have been proposed in the early years of the nineties of the $20^{th}$ century. The above conventional container inspection system is devised as follows. Stationary accelerator which produces high energy x-ray as radiation source and stationary array detectors which receive x-ray passing through the container are mounted in an inspection passage which is capable of shielding radiation beams. A vehicle carrying the container which is pulled by a special pulling device so as to pass by the inspection passage. When the container passes x-ray, x-ray will transmit through the container and incident on the detectors. As a result, the density distribution of the objects contained in the container is presented in accordance with the variation of the intensity of x-ray. Then, the intensity of x-ray is converted into a corresponding gray degree of an image so that a perspective view of the objects contained in the container can be obtained.

As the technique of imaging by radiation is widely used at present, it is used for the train inspection system more and more. In a train inspection system, an inspecting device is generally mounted on the ground, namely, a radiation source is mounted on one side of the track, and a detector bracket is mounted on the other side of the track. The image of the objects contained in the train is obtained by use of the technology of imaging by radiation.

However, as users' demands are continuously raised concerning the train inspection system, the speed for performing the train's inspection is required to be continuously improved, especially in the case that the trains with heavy loads run along wretched tracks, vibration from the base of the track gets stronger and stronger. Accordingly, the conventional device as arranged above does not meet the demands for the inspection of the train, and the strong vibration sometimes interferes with the imaging by scanning, thus directly deteriorating the imaging by scanning.

SUMMARY OF THE INVENTION

The present invention is made to solve one or more aspects of the prior arts as mentioned above. Accordingly, an object of the present invention is to provide a scanning arm for the train inspection system and a train inspection system by imaging through radiation having the scanning arm. With the train inspection system of the present invention, interference to the imaging due to vibration of the groundwork for the track can be avoided, and accuracy of imaging by scanning can be improved.

In order to achieve one or more aspects of the objects as stated above, the present invention provides a scanning arm used for a train inspection system by imaging through radiation, comprising: a rigid middle inclining section: an upper horizontal section located at an upper end of the middle inclining section, said upper horizontal section is supported on a construction base: a lower horizontal section located at a lower end of the middle inclining section, said lower horizontal section is supported on the construction base; vibration damping elements, said vibration damping elements are respectively arranged between the upper horizontal section and the construction base, and between the lower horizontal section and the construction base.

Preferably, said vibration damping element is a damping spring or an elastic rubber pad or similar element.

According to another aspect of the present invention, the present invention provides a train inspection system by imaging through radiation, comprising: a scanning arm, including: a rigid middle inclining section; an upper horizontal section and a lower horizontal section which are located at upper and lower ends of the rigid middle inclining section respectively and supported on a construction base; and vibration damping elements arranged between the upper horizontal section and the construction base, and between the lower horizontal section and the construction base; a detector bracket with detector arrays mounted thereon, wherein the top of the detector bracket is perpendicularly fixedly connected with said upper horizontal section; a radiation source connected with a supporting abutment, wherein said supporting abutment is fixedly connected with the lower horizontal section to be suspended from the lower horizontal section; a calibration device, said calibration device is fixed on the horizontal ground and faces x-ray emitted from the radiation source; a front collimator, said front collimator is fixedly connected with said middle inclining section so as to be suspended from said rigid middle inclining section, and said front collimator faces said calibration device so that the calibration device is located between the front collimator and the radiation source; a rear collimator, said rear collimator is fixedly connected with said middle inclining section so as to be suspended from said rigid middle inclining section, said rear collimator faces said front collimator and the front collimator is located between the calibration device and the rear collimator; wherein the sector-shaped x-ray emitted from the radiation source penetrate through the calibration device, the front collimator, the rear collimator and the train to be inspected sequentially so as to be received by the detector array provided on the detector bracket.

Preferably, said radiation source is a linear electron accelerator or an isotope source.

In the train inspection system by imaging through radiation, the radiation source, the front collimator, the rear collimator and the detector bracket with detector arrays are connected to the scanning arms while the scanning arm is located a position away from the track, and vibration damping elements are provided between the scanning arms and the construction base. As a result, it is possible to reduce the vibration impact on the scanning arm from the track, thus greatly decreasing efficiency of the vibration. Even if residual vibration is remained, the components mounted on the scanning arm are vibrated in the same frequency as that of the vibration. As such, the imaging by the scanning is not adversely affected. Compared with the prior arts, the train inspection system by imaging through radiation is advantageous in reasonable designing, good adaptation, reliable construction, stable imaging and reduced occupied area. Accordingly, the train inspection system by imaging through radiation of the present invention is advantageously applicable to inspection of trains for the customs.

DETAILED DESCRIPTION OF THE PREFERRED EMBODIMENTS

Figure 1:
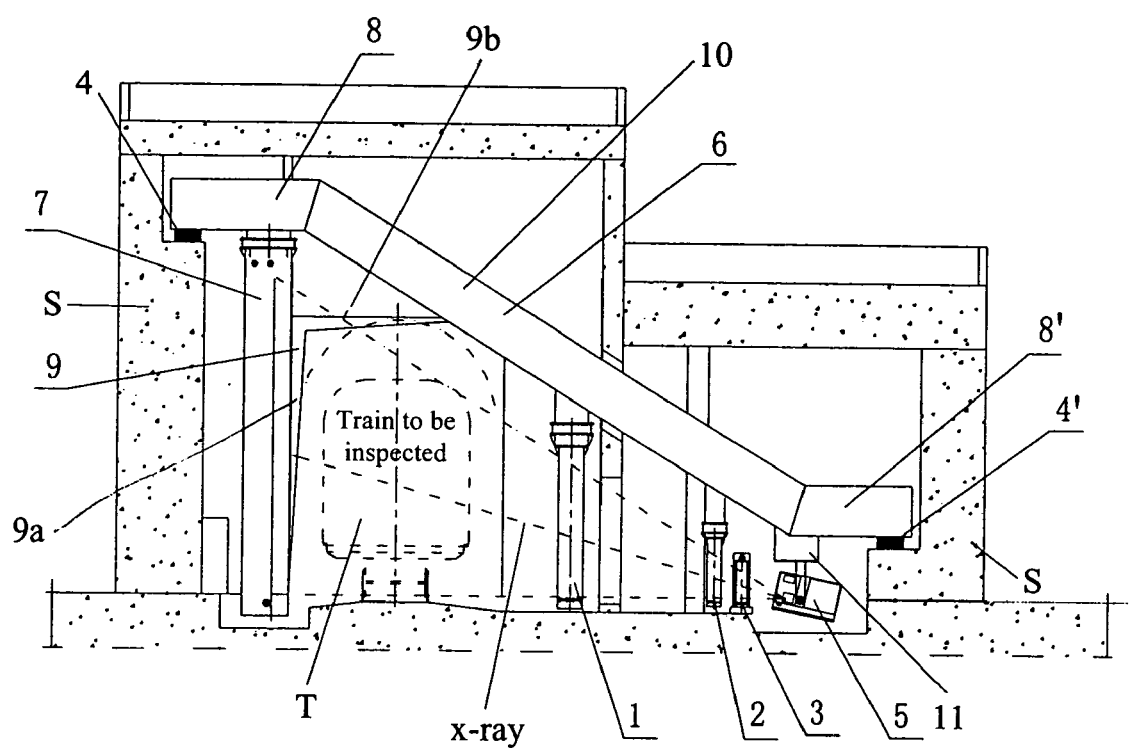
FIG. 1 is a configuration diagram of a train inspection system by imaging through radiation having a scanning arm according to an embodiment of the present invention.

A preferred embodiment of the present invention will be described hereinafter in detail with reference to the attached drawings, wherein the like reference numerals refer to the like elements throughout the specification. The present invention may, however, be embodied in many different forms and should not be construed as being limited to the embodiment set forth herein; rather, this embodiment is provided so that the present disclosure will be thorough and complete, and will fully convey the concept of the invention to those skilled in the art.

As shown in FIG. 1, the train inspection system by imaging through radiation of the present invention includes a radiation source 5, such as a linear electron accelerator or an isotope source, a calibration device 3, a front collimator 2, a rear collimator 1, a detector bracket 7 with detector arrays mounted thereon, and a scanning arm 10. The scanning arm 10 includes a rigid middle inclining section 6, an upper horizontal section 8 located at an upper end of the middle inclining section 6 and a lower horizontal section 8' located at a lower end of the rigid middle inclining section 6. The upper horizontal section 8 and the lower horizontal section 8' are supported on the construction base S along both sides of the track, and vibration damping elements 4 and 4' are arranged between the upper and lower horizontal sections and the construction bases S respectively.

The damping elements 4 and 4' can be a damping spring or an elastic rubber pad or other similar elements. The upper horizontal section 8 of the scanning arm 10 is also fixedly connected with the top of the detector bracket 7, and the lower horizontal section 8' is fixedly connected with a supporting abutment 11 of said radiation source 5 so that the radiation source 5 is suspended from the lower horizontal section 8' by the supporting abutment 11. A angle frame 9 is provided in a vertical plane where the detector bracket 7 faces the middle inclining section 6 of the scanning arm 10 for reinforcing the rigidity of the system. The first arm 9a of the angle frame 9 is fixed on the vertical plane of the detector bracket 7 and a free end of the second arm 9b of the angle frame 9 supports the middle inclining section 6. X-ray emitted from the radiation source 5 faces the calibration device 3 which is fixed on the horizontal ground, and the calibration device 3 sequentially faces the front collimator 2 and the rear collimator 1 which are fixedly connected with the middle inclining section 6 of the scanning arm 10. As a result, the sector-shaped x-ray emitted from the radiation source 5 penetrate through the calibration device 3, the front collimator 2, the rear collimator 1, the train to be inspected T sequentially and are received by the detector arrays mounted on the detector bracket 7.

In operation, the radiation source 5, the front collimator 2 and the rear collimator 1 are sequentially connected on the scanning arm 10 and located on one side of the track, and the detector bracket 7 with the detector arrays is located on the other side of the track. When the train T to be inspected passes through the train inspection system by imaging through radiation along the track, after the sector-shaped x-ray emitted from the radiation source 5 penetrate through the front collimator 2, the rear collimator 1, the train T to be inspected, x-ray is received by the detector arrays mounted on the detector bracket 7. In this way, the scanning inspection on the train T to be inspected by imaging through radiation is carried out.

In the train inspection system by imaging through radiation of the present invention, as damping elements 4 and 4' are respectively provided between the upper horizontal section 8 and the lower horizontal section 8' of the scanning arm 10 and the construction base S, vibration of the scanning arm 10 is effectively reduced. As a result, efficiency and accuracy of imaging by radiation have been improved. In addition, the damping element 4 or 4' is not limited to be a damping spring or an elastic rubber pad but can be any suitable damping elements.

Although a preferred embodiment has been shown and described, it should be noted that the above embodiment is considered to be illustrative rather than limitative. The protection scope of the present invention is defined in the appended claims and their equivalents thereof. It would be appreciated by those skilled in the art that modifications, changes and replacement may be made in these embodiments without departing from the principles and spirit of the invention.

The invention claimed is:

1. A train inspection system by imaging through radiation, comprising:
    a scanning arm including: a rigid middle inclining section; an upper horizontal section and a lower horizontal section which are located at upper and lower ends of the rigid middle inclining section respectively and supported on a construction base; and vibration damping elements arranged between the upper horizontal section and the lower horizontal section and the construction base;
    a detector bracket with detector arrays mounted thereon, wherein the top of the detector bracket is perpendicularly fixedly connected with said upper horizontal section;
    a radiation source connected with a supporting abutment, wherein said supporting abutment is fixedly connected with the lower horizontal section to be suspended from the lower horizontal section;
    a calibration device, said calibration device is fixed on the horizontal ground and faces x-ray emitted from the radiation source;
    a front collimator, said front collimator is fixedly connected with said middle inclining section so as to be suspended from said rigid middle inclining section, and said front collimator faces said calibration device so that the calibration device is located between the front collimator and the radiation source;
    a rear collimator, said rear collimator is fixedly connected with said middle inclining section so as to be suspended from said rigid middle inclining section, said rear collimator faces said front collimator so that the front collimator is located between the calibration device and the rear collimator;
    wherein the sector-shaped x-ray emitted from the radiation source penetrate through the calibration device, the front collimator, the rear collimator and the train to be inspected sequentially so as to be received by the detector arrays provided on the detector bracket.

2. The train inspection system by imaging through radiation according to claim 1, wherein said vibration damping element is a damping spring.

3. The train inspection system by imaging through radiation according to claim 1, wherein said vibration damping element is an elastic rubber pad.

4. The train inspection system by imaging through radiation according to any one of claims 1-3, wherein said radiation source is a linear electron accelerator or an isotope source.

* * * * *